(12) United States Patent
Windschauer et al.

(10) Patent No.: US 9,764,168 B2
(45) Date of Patent: *Sep. 19, 2017

(54) TASTE MASKING COMPOSITIONS AND EDIBLE FORMS THEREOF

(75) Inventors: Robert J. Windschauer, Largo, FL (US); Teresa T. Virgallito, Beavercreek, OH (US)

(73) Assignee: ACME SPECIALTY PRODUCTS, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,520

(22) Filed: Apr. 25, 2012

(65) Prior Publication Data

US 2012/0321727 A1 Dec. 20, 2012

Related U.S. Application Data

(60) Provisional application No. 61/480,102, filed on Apr. 28, 2011.

(51) Int. Cl.

| | | |
|---|---|---|
| *A61K 9/20* | (2006.01) | |
| *A61Q 11/00* | (2006.01) | |
| *A61K 8/86* | (2006.01) | |
| *A61K 8/02* | (2006.01) | |
| *A23L 27/00* | (2016.01) | |
| *A61K 36/28* | (2006.01) | |

(52) U.S. Cl.
CPC .............. *A61Q 11/00* (2013.01); *A23L 27/79* (2016.08); *A61K 8/0216* (2013.01); *A61K 8/86* (2013.01)

(58) Field of Classification Search
CPC ........ A61Q 11/00; A61K 8/86; A61K 8/0216; A23L 27/79
USPC ................................................. 424/465, 737
See application file for complete search history.

(56) References Cited

U.S. PATENT DOCUMENTS

| | | | |
|---|---|---|---|
| 3,644,653 | A | 2/1972 | Tcheiltcheff |
| 4,296,255 | A | 10/1981 | Roswell et al. |
| 6,303,372 | B1 | 10/2001 | Kaufmann |
| 2001/0022964 | A1 | 9/2001 | Leung et al. |
| 2003/0099692 | A1 | 5/2003 | Lydzinski et al. |
| 2003/0224090 | A1* | 12/2003 | Pearce et al. ............. 426/89 |
| 2004/0043134 | A1 | 3/2004 | Corriveau et al. |
| 2004/0086546 | A1 | 5/2004 | Maxwell et al. |
| 2004/0096569 | A1 | 5/2004 | Barkalow et al. |
| 2004/0258733 | A1 | 12/2004 | Maxwell et al. |
| 2005/0036977 | A1 | 2/2005 | Gole et al. |
| 2006/0024335 | A1 | 2/2006 | Roger |
| 2006/0147516 | A1 | 7/2006 | Habib et al. |
| 2007/0051741 | A1 | 3/2007 | Gaonkar et al. |
| 2007/0072939 | A1 | 3/2007 | Kupper |
| 2010/0189768 | A1 | 7/2010 | Andersen et al. |
| 2010/0285178 | A1 | 11/2010 | Labbe et al. |

FOREIGN PATENT DOCUMENTS

| | | |
|---|---|---|
| CN | 1140091 | 1/1997 |
| EP | 1693057 | 8/2006 |
| FR | 1572332 | 6/1969 |
| TW | 200738152 | 10/2007 |
| WO | 97/02273 | 1/1997 |
| WO | 2004/019885 | 3/2004 |

OTHER PUBLICATIONS

International Search Report and Written Opinion, International Application No. PCT/US2011/038987 (Feb. 17, 2012).
Goel, H. et al., "Orally Disintegrating Systems: Innovations in Formulation and Technology," Recent Patents on Drug Delivery & Formulation, vol. 2, No. 3, pp. 258-274 (2008).
AU, Patent Examination Report No. 1; Australian Patent Application No. 2011366911 (Jun. 4, 2015).
EP, First Examination Report and Opinion; European Patent Application No. 11729202.9 (Jun. 2, 2015).
TW, Search Report; Taiwanese Patent Application No. 101115048 (Jan. 13, 2016).
Sharma, S., & Lewis, S.; "Taste masking technologies: a review"; International Journal of Pharmacy and Pharmaceutical Sciences; vol. 2, Issue 2; pp. 6-13 (Jan. 15, 2010).
風一樣的心情 (Nickname or ID of User) "Meiji Collagen Generation 3 . . . After eating . . . " Fashion Guide Beauty Forum, Website: http://forum.fashionguide.com.tw/post_list.php?topic_id=345009 (Feb. 5, 2009).
Specifications: "Natural Masking Agent for Animal Protein O.S. #5187", by GBS & Associates (Apr. 5, 2016).

* cited by examiner

*Primary Examiner* — Adam C Milligan
(74) *Attorney, Agent, or Firm* — Thompson Hine LLP

(57) ABSTRACT

Disclosed are edible formulations, for example, edible films and gummi confectioneries, that mask the taste of semen. The films and confectioneries include a composition that upon activation in the oral cavity provides a lasting taste masking effect that endures for up to 20 minutes. The composition includes a film former or gelling agent, an effective amount of a protein masker, and an effective amount of a bitter masker. The composition may also include a flavoring agent, sweetening agents, and sensates.

8 Claims, No Drawings

TASTE MASKING COMPOSITIONS AND EDIBLE FORMS THEREOF

RELATED APPLICATIONS

This application claims the benefit of U.S. Provisional Application No. 61/480,102, filed Apr. 28, 2011.

FIELD OF THE INVENTION

The present invention relates to taste masking compositions, in particular, edible forms of the taste masking composition such as films and gummi confectioneries.

BACKGROUND OF THE INVENTION

Because of the unpleasant taste of many pharmaceuticals or nutritional supplements, flavorings alone or in combination with sweetening agents have been employed to improve taste and palatability. Flavorings and sweetening agents, however, are not satisfactorily effective against bitter tasting substances and/or actives.

Various delivery vehicles for taste masking or taste-modifying the delivery of pharmaceuticals or nutritional supplements have been employed, such as flavored liquid suspensions, coatings on pharmaceutical tablets and/or capsules, and even dissolvable films. However, in each of these situations, the substance to be masked is present at the time of delivery of the taste masking or modifying substance. For example, dissolvable films have been used to deliver pharmaceutical actives to children and to deliver breath-freshening agents such as menthol. In both instances, the substance to be taste-masked was either present in the formulation itself or was already present, which makes developing taste masking formulations easier.

Semen is a semi-variable, yet specific chemical composition that includes at least one bitter tasting substance. Semen typically includes approximately 150 mg of protein, 11 mg of carbohydrate, 6 mg of fat, 3 mg of cholesterol, and trace amounts of ascorbic acid, calcium, chlorine, choline, citric acid, creatine, deoxyribonucleic acid, fructose, glutathione, hyaluronidase, inositol, lactic acid, magnesium, nitrogen, phosphorus, potassium, purine, pyrimidine, pyruvic acid, selenium, sodium, sorbitol, vitamin B12, and zinc. One factor that makes semen variable is the diet of the individual.

Semen is a complex composition for which to formulate a taste masking composition, especially to make it universally effective on a semi-variable composition. Furthermore, the formulation must account for the unpredictable timing of the delivery of the semen, which depends upon sexual stimulation. These factors complicate the formulation of an effective composition and a delivery vehicle that can provide the needed taste masking effect at the appropriate time.

SUMMARY OF INVENTION

In one aspect, edible compositions are disclosed herein that are capable of providing up to twenty minutes of taste masking effectiveness to mask the taste of semen. The composition may be in the form of any suitable delivery vehicle. In one embodiment, the delivery vehicle is a film. In another embodiment, the delivery vehicle is a gummi confectionery. While the discussion herein focuses on the film and gummi confectionery delivery vehicles, the formulations are not so limited.

Both the edible film and the edible gummi confectionery, upon activation in saliva in the oral cavity, provide a lasting taste masking effect that endures for about 5 to 20 minutes. The enduring taste masking effect is possible because of the presence of at least one protein masking agent and at least one bitter masking agent. The protein masking agent constitutes about 0.01% to about 16% dry weight of either the edible film or the edible gummi confectionery, and the bitter masking agent may constitute about 0.1% to 7% dry weight thereof.

Both the edible film and the edible gummi confectionery may include a flavoring agent, a sensate, and/or a sweetening agent. The flavoring agent may constitute about 0.1% to about 30% dry weight, the sensate may constitute about 0.1% to about 25% dry weight, and the sweetening agent may constitute about 1% to about 20% dry weight of either the edible film or the edible gummi confectionery.

In another embodiment, edible compositions capable of providing up to twenty minutes of taste masking effectiveness are disclosed that include a delivery vehicle, a physiological effective amount of a protein masking agent, a physiological effective amount of a bitter masking agent, and a physiological effective amount of a sensate. The edible composition may also include a flavoring agent and a sweetening agent.

In another aspect, methods of making an edible film for masking the taste of semen are disclosed.

In another aspect, methods of making an edible gummi confectionery for masking the taste of semen are disclosed.

DETAILED DESCRIPTION OF INVENTION

To address the complex composition of semen and the time sensitive nature of the delivery thereof, edible compositions were developed that are capable of providing up to twenty minutes of taste masking effectiveness for masking the taste of semen. The taste masking effectiveness may be formulated to last for about five to about twenty minutes. In another embodiment, the taste masking effectiveness may last for about seven to about fifteen minutes.

The edible compositions disclosed herein are designed to be placed in a user's mouth (or oral cavity) for chewing and/or dissolving, depending upon the delivery vehicle. Once chewed and/or dissolved, the formulation's ingredients such as one or more taste masking agents, a sensate, a flavoring agent, or a sweetening agent act upon the taste receptors in the oral cavity, including those around the tongue, on the soft palate at back roof of the mouth, and even the epiglottis, to provide a physiological effect of lasting taste masking effectiveness. In one embodiment, the delivery vehicle of the edible taste masking composition is as an edible film. In another embodiment, the delivery vehicle of the edible composition is as an edible gummi confectionery. The delivery vehicle may also be, but is not limited to a chewable tablet, a liquid carrier, a hard confectionery, a gel confectionary, a foam confectionary, a chewing gum, a dissolvable tablet, and a powder confectionary.

Methods for making such delivery vehicles are known and can be adapted for by one of skill in the art to provide a delivery vehicle for the taste masking compositions disclosed herein. Various methods for forming orally disintegrating tablets, whether by applying heat or a non-heat process, orally disintegrating films, chewing gums, particles and/or microencapsulated compositions are described in the article "Orally Disintegrating Systems: Innovations in Formulation and Technology" by Goel et al. in *Recent Patents on Drug Delivery & Formulation*, 2008, Vol. 2, No. 3, pages 258-274. The article and the patents referenced therein teach how to make such delivery vehicles.

The delivery vehicles described in the Goel et al. article are directed to the delivery of an active pharmaceutical ingredient. The edible compositions herein, regardless of the delivery vehicle, are free of an active pharmaceutical ingredient. As used herein, the phrase "active pharmaceutical ingredient" or "API" means any substance or mixture of substances intended to be used in the manufacture of a drug (medicinal) product and that, when used in the production of a drug, becomes an active ingredient of the drug product. Such substances are intended to furnish pharmacological activity or other direct effect in the diagnosis, cure, mitigation, treatment, or prevention of diseases or other ailments. The taste masking agents, sensates, flavoring agents, and sweeteners that individually may contribute to the taste masking effect are not active pharmaceutical ingredients as defined herein.

The edible compositions are a taste masking delivery system that has a synergistically effective amount of taste maskers and sensates that dissolve in the oral cavity and upon dissolution are deposited on the tongue. The masking agents and sensates (and optionally one or more sweeteners) interact with taste receptors on the tongue to provide taste masking effectiveness that masks the taste of semen (which is independently delivered to the oral cavity). The taste masking molecules interacts with taste receptors on the tongue and provide a sensation, which is the result of signal transduction from the receptor organs for taste, commonly known as taste buds. These taste buds contain very sensitive nerve endings, which produce and transmit electrical impulses via the seventh, ninth and tenth cranial nerves to those areas of the brain, which are devoted to the perception of taste. The masking agents in the disclosed compositions effectively turn "off" the taste buds for a period of about 20 minutes, i.e., long enough for fellatio. The edible compositions disclosed herein are formulated with taste masking agents and sensates that are not irritating to the skin (in particular, that of the penis) as will be explained in more detail herein.

Edible Films

The edible film may be referred to as an "edible thin film." As used herein, "edible thin films" refers to compositions that include a film-former substrate and are designed to adhere to at least a portion of the oral cavity of a consumer and rapidly dissolve therein. "Rapidly dissolve" means that the substrate dissolves in less than 20 seconds, preferably less than 15 seconds and most preferably less than 10 seconds. To "dissolve" means to substantially lose the shape and form of the substrate. An example of an edible thin film product is the Listerine® PocketPaks™ oral care strip sold by Pfizer.

In addition to the film-former, the edible thin films for masking the taste of semen include a physiological effective amount of a protein masking agent and a physiological effective amount of a bitter masking agent. The term "masking agent" as used herein, with respect to all the compositions disclosed herein, also encompasses substances that may be classified as taste-receptor blockers. The edible thin films may include a sensate, a flavoring agent, and/or a sweetening agent. It is understood that one or more of any of these individual ingredients may be used in a formulation. For example, the composition may include one protein masking agent, two bitter masking agents, three sensates, one flavoring agent, and one sweetening agent as shown in Example 1 below.

Any suitable water-soluble, film-former can be used to produce an edible thin film product. Suitable film-formers include but are not limited to water-soluble non-starch polysaccharides such as carboxymethylcellulose (CMC), methylcellulose, hydroxypropylmethylcellulose (HPMC), guar gum, locust bean gum, xanthum gum, carrageenan, algins, propylene glycol, levan, elsinan, pullulan, pectins, chitosan, and gum arabic; native starches such as corn starch, waxy maize starch, high-amylose corn starch, potato, tapioca, rice and wheat starch; modified starches such as those that have been acid modified, bleached, oxidized, esterified, etherified, crosslinked, and treated enzymatically; starch hydrolyzed products such as maltodextrin; protein such as albumen, gelatin, casein, salts of casein, whey, wheat gluten, zein, and protein derived from soybeans; polymers such as polyvinyl pyrrolidone, methycrylate copolymer, and carboxyvinyl copolymers alone or in any combination. In one embodiment, the concentration of the film-forming agent constitutes between 5% to about 60% by dry weight, or 20% to about 40% by dry weight of the final film composition.

If it is desired to use lower levels of film forming agents, softeners can also be employed to ensure the flexibility of the film, thereby reducing brittleness. The softeners, which are also known as plasticizers, may include tallow, hydrogenated tallow, hydrogenated and partially hydrogenated vegetable oils, cocoa butter, sorbitol and other polyols, including polyoxyethylene sorbitan monooleate, glycerin, polyethylene glycol, propylene glycol, invert sugars, corn syrup, lecithin, hydrogenated lecithin, mono-, di- and triglycerides, acetylated monoglycerides, fatty acids (e.g. stearic, palmitic, oleic and linoleic acids), Polyoxyethylene (80) sorbitan monooleate, and combinations thereof. In one embodiment, the softener may constitute 0% to about 20% by dry weight of the film, or about 2% to about 10% by dry weight of the film.

The film composition includes one or more protein masking agents that are not irritating to the skin (in particular, that of the penis). Protein masking agents are generally oil and water soluble compositions that coat the taste receptors and makes them non-responsive to the unpleasant taste of proteins and/or flavors selected to deceive the senses into associating the bitterness with an acceptable substance such as chocolate or a fruit flavor. In the compositions disclosed herein, the protein masking agent is present in a physiological effective amount to mask the protein-based components of semen. In one embodiment, the protein masking agent constitutes about 0.01 to about 16% dry weight of the film. In another embodiment, the protein masking agent constitutes about 0.05 to about 10% dry weight of the film.

One suitable protein masking agent is GSB Natural Masking Agent for Animal Protein O.S. #5187, which is an oil soluble liquid flavoring that masks the unpleasant taste of protein notes in a composition, has a sausage-like odor and flavor, is a light to medium yellow colored free-flowing liquid, has a specific gravity (density) at 25° C. of 0.899 to 0.959 g/ml, and includes refined coconut oil as a non-flavor ingredient. Other flavors may mask the unpleasant taste of proteins and other bitter-tasting ingredients. For examples, vanilla, chocolate, coffee and caramel flavors may be used to mask protein, in particular the bitterness often associated with protein. Certain flavors are not suitable as protein or bitter masking agent, including chamomile, mint, dandelion, angelica, horehound, milk thistle, peppermint, licorice, citrus peel, green apple, vinegar, yarrow, ginger, apricot seed, cherry seed, grapefruit, cinnamon bark or for inclusion in the formulations because they can irritate and/or burn the skin, including cherry flavoring (artificial and/or natural), amyl acetate, amyl alcohol, annatto bixine, benzaldehyde, benzyl acetate, cinnamyl formate, acetonitrile, benzyl chloride, cinnamaldehyde, limonene, menthol, and eucalyptus.

Acids found naturally in fruit such as malic acid (apple's primary acidulant) and citric acid (prevalent in strawberries) deceive the senses into associating the bitterness with the fruit used, rather than the protein. These acids do not mask the protein. They merely make the brain think the bitterness is from an acceptable source and should not be considered to be a protein masker as used herein.

In another embodiment, a combination of soy protein isolate and pectin can be added to the composition to taste masker a casein hydrolysate. Solae's Supro soy protein isolate (SPI) and CP Kelco's Genu low-methoxy pectin are examples of a suitable combination.

One or more bitter masking agents may be present in the film in an amount to mask the bitter taste of semen, especially when combined with the protein masking agent. In one embodiment, the bitter masking agent constitutes about 0.1 to 7% dry weight of the film. In another embodiment, the bitter masking agent constitutes about 0.5 to 5% dry weight of the film. The bitter masking agents should be one that is not irritating to the skin (in particular, that of the penis).

A particularly effective class of compounds which can function as a bitter masking agent are hydrogenated, ethoxylated glycerol esters. These types of compounds are commercially available and may be formed in a well-known manner, namely by the ethoxylation of glycerol. One commercially available compound which works as a bitter masking agent is sold by the BASF Company under the trade name CREMOPHOR®, including CREMOPHOR® 40 and CREMOPHOR® 60 hydrogenated ethoxylated castor oils. Other suitable bitter masking agent or blocker include, but are not limited to adenosine 5'-monophosphate, thymidine 5' monophosphate, adenosine 5' diphosphate, adenosine 3' monophosphate, adenosine 5'-succinate, adenosine 5' triphosphate, adenosine 2' monophosphate, 5'-cytidylic acid, inosinic acid. Some commercially available bitter masking agents, include Ottens BITTERNESS BLOCKERS® NI-1915-A and Firmenich SWEETNESS ENHANCER® 598960 TP 1054, Quest NATURAL BITTER BLOCKERS®, Fontarome MAG-NIFIQUE®, Givaudan MASKING FLAVOR®, WILD FAE®, GSB Natural Soy Masking Flavor (Milk Type) P.F. #8236, GSB Natural Sweetness Masking Flavor W.S. #7895, GSB Natural Masking Agent Flavor W.S. #5206, GSB Natural Masking Flavor W.S. #6500, GSB Natural Sugar Extender Type Flavor W.S. #8490, Mother Murphy NAT. MASKING TYPE FLAVOR 188505, Mother Murphy NAT. MASKING FLAVOR 155122, Mother Murphy NAT. BITTER MASKING FLAVOR 2111197, Mother Murphy N&A MASKING FLAVOR, W.S. 2110085, Taste Advantage Natural Flavor-Mouthfeel Enhancer Type 1 in EtOH, Biogapress™ Vegetal BM 297 ATO Glyceryl dipalmitostearate, Glycerol monostearate (type I) EP, Mono and diglycerides NF, Precirol® ATO 5 Glycerol distearate (type I) EP, Glyceryl distearate NF, other commercially available bitter masking agents, and combinations thereof.

The compositions disclosed herein may also include a variety of sensates that are not irritating to the skin (in particular, that of the penis). The sensate may be a physiological cooling agent, a physiological warming agent, or a physiological tingling agent, each of which are effective on the mucous membranes of the oral cavity. The formulations disclosed herein may include one or more of each type of sensate and/or combinations thereof. The total sensate content of an edible thin film may constitute about 0.1 to about 25% dry weight of the film, or about 1% to about 15% by dry weight of the film.

As used herein, "physiological cooling agent" does not include traditional flavor-derivatives such as menthol or menthone. Suitable physiological cooling agents are those that do not have a perceptible flavor of their own, but simply provide a cooling effect. The physiological cooling agent may constitute about 0.1 to about 25% dry weight of the film, or about 1% to about 15% by dry weight of the film. The physiological cooling agents include, but are not limited to, isopulegol, N-substituted-p-menthane-3-carboxamides, acyclic tertiary and secondary carboxamides, 3-1-menthoxy propan-1,2-diol, p-menthane-3,8-diol, monomenthyl glutarate, and monomenthyl saccidate, alone or in any combination. The N-substituted-p-menthane-3-carboxamides, such as N-ethyl-p-menthane-3-carboxamide, and trimethyl isopropyl butanamide are both commercially available under the trademark Winsense® from LyondellBasell Flavors & Fragrances, LLC, for example as WS-3 and WS-23, respectively. Monomenthyl glutarate is commercially available under the trademark Ultracool 2 from IFF (Netherlands).

Other physiological cooling agents include, but are not limited to, 3-(1-menthoxy)-2-methylpropane-1,2-diol, p-menthane-2,3-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, and menthyl pyrrolidone carboxylate.

The compositions of the present invention may include a warming agent alone or in addition to other sensates such as cooling agents and/or tingling agents. The warming agent is preferably present in a physiologically effective amount. The warming agent may constitute about 0.001 to about 10%, or from about 0.005 to about 5%, or from about 0.01 to about 1% by dry weight of the film.

Suitable physiological warming agents include, but are not limited to, vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, cinnamic aldehyde, phosphate derivatives thereof, and mixtures thereof. The phosphate derivatives mentioned are those described in WO 97/02273. A commercial example of a suitable warming agent for use herein is Optaheat (Symrise, Germany).

The compositions herein may also include a physiological tingling agent alone or in addition to the cooling agent and/or the warming agent. As used herein, "physiological tingling agent" refers to agents which trigger a tingling, stinging, or numbing sensation in the oral cavity. These tingling agents may be selected from a plethora of compounds (plant extracts or synthetic compounds) that are known in the art to provide a tingling sensation and are used accordingly in a number of food products. Such plant extracts include extracts from pepper, onion, garlic, radish, horseradish, mustard, chili, ginger etc. These may also include, but are not limited to Jambu Oleoresin or para cress (*Spilanthes* sp.) in which the active ingredient is Spilanthol; Japanese pepper extract (*Zanthoxylum peperitum*), including the ingredients known as Saanshool-I, Saanshool-II and Sanshoamide; black pepper extract (*piper nigrum*), including the active ingredients chavicine and piperine; Echinacea extract; Northern Prickly Ash extract; and red pepper oleoresin.

A variety of flavoring agents can also be added to the edible thin films. Any suitable amount and type of artificial and/or natural flavoring agents can be used in any sensorially acceptable fashion. However, the word "suitable" as used herein means that the flavoring agent does not cause irritation and/or burning to the skin. The flavoring agent may constitute about 0.1% to about 30%, or about 1 to about 20%, or about 5% to about 15% dry weight of the film. The flavoring agent can include, for example, essential oils, synthetic flavors or mixtures including but not limited to oils derived from plants and fruits such as citrus oil, fruit essences, peppermint oil, spearmint oil, other mint oils, clove oils, oil of wintergreen, anise and the like, or combinations thereof. Other suitable flavoring agents include chocolate flavors, cocoa powder, vanilla, vanillin and ethyl vanillin.

Certain flavors are not suitable for inclusion in a tasking masking agent used during fellatio because they can irritate and/or burn the skin. These flavors include cherry flavoring (artificial and/or natural), amyl acetate, amyl alcohol, annatto bixine, benzaldehyde, benzyl acetate, cinnamyl formate, acetonitrile, benzyl chloride, cinnamaldehyde, limonene, thymol, menthol, and eucalyptus.

The flavor can be enhanced and distributed evenly throughout the product by emulsification. Any suitable amount and type of natural and/or synthetic food-grade emulsifier can be used. For example, the emulsifier can include lecithin, food-grade non-ionic emulsifiers, such as a starch or modified starch, fatty acids ($C_{10}$-$C_{18}$), mono and diacyl glycerides, ox bile extract, polyglycerol esters, polyethylene sorbitan esters, propylene glycol, sorbitan monopalmitate, sorbitan tristerate, other like emulsifiers or combinations thereof.

The flavors are emulsified using any suitable emulsification process, such as mechanical processing, vigorous stirring, intense pressure fluctuations that occur in turbulent flow such as homogenization, sonification, colloid milling and the like.

Sweetening agents may also be used in the edible thin films. The sweetening agents may include sugar sweeteners and/or sugarless sweeteners, including high intensity artificial sweeteners. The sugar sweeteners generally include saccharide-containing components including, but not limited to, sucrose, dextrose, maltose, dextrin, invert sugar, fructose, levulose, galactose, corn syrup solids, vanilla syrup, and the like, alone or in any combination. Sugarless sweeteners include, but are not limited to sugar alcohols, such as sorbitol, mannitol, xylitol, isomalt, hydrogenated starch hydrolysates, maltitol, and the like, alone or in any combination. The high intensity artificial sweeteners include, but are not limited to, sucralose, aspartame, N-substituted APM derivatives such as neotame, salts of acesulfame, alitame, saccharin and its salts, cyclamic acid and its salts, glycyrrhizin, dihydrochalones, thaumatin, monellin, and the like, alone or in any combination. Combinations of sugar and/or sugarless sweeteners may be used in the film product in any suitable amount. In one embodiment, the sweetening agent constitutes about 1% to about 20%, or about 2% to about 15% dry weight of the film.

If desired, the edible thin film formulations of the present invention can also include colorants or coloring agents which can be used in any suitable amount to produce a desired color. Further, the edible thin films of the present invention may have multi-colored patterns and/or other related designs or shapes to produce color contrasts. Coloring agents can include, for example, natural food colors and dyes suitable for food, drug, and cosmetic applications. The colorants are typically known as FD&C dyes and lakes such as FD&C Blue No. 1, FD&C Blue No. 2, FD&C Green No. 3, FD&C Yellow No. 5, FD&C Yellow No. 6, FD&C Red No. 3, FD&C Red No. 33, FD&C Red No. 40, and combinations thereof. The coloring agents may constitute about 0.01% to about 1% dry weight of the edible thin film.

Depending on the ingredients being used to make the edible thin film product, preservatives may also be employed to ensure the safety and quality of the film. Suitable preservatives include, but are not limited to, sorbic acid, sodium benzoate, potassium sorbate, methyl p-hydroxybenzoate, sodium propionate, and propyl p-hydroxybenzoate alone or in any combination. In addition, suitable antioxidants can also be utilized. Preservatives or the antioxidants may be present in the composition as 0.01% to about 1% dry weight of the edible thin film.

Edible thin films can be formed by a variety of different processes. One such process is as follows: (1) an aqueous solution is formed by blending film-forming materials together with water and are agitated until the powdered materials are mostly hydrated and a few lumps are present; (2) to this mixture, protein masking agents, bitter masking agents, plasticizers, softening agents, colors, sweeteners, cooling agents, flavoring agents, and other ingredients are blended together to form a homogeneous solution; and (3) this solution is then cast onto a suitable carrier, and dried to form a film.

The carrier material should be impermeable to the film coating, allowing the film coating to disperse evenly onto the carrier. This also allows for ease of removal of the plastic film from the carriers. Examples of suitable carriers include plastic or polyester films, polypropylene, polycarbonate, non-siliconized polyethylene terephthalate film, non-siliconized Kraft paper, polyethylene impregnated Kraft paper, metal belts, voltage or corona treated belts, drum dryers, and polytetrafluoroethylene-impregnated glass fabric. Multiple carriers may be employed to create a multi-layered film product. The carriers may be coated with a release coating.

It has been found that a particularly preferred method of casting the film on the carrier may be through use of a slot die extrusion. By use of multiple extruders and appropriately constructed dies, it is possible to add multiple color stripes or designs to the product. It is also possible to oscillate the die head to produce wavy lines on the product. The resulting films can be laminated to produce various visual effects.

The casting of the solution onto a suitable carrier material can be performed using any conventional coating technique. Examples of coating techniques include spraying, dipping, comma coaters, knife over plate, roll over roll, reverse roll, slot die extrusion, and various extrusion techniques. Film thickness can be controlled by adjusting the gap on the coating head, or by applying the desired amount of the solution onto the substrate/carrier.

It should be noted that no particular limitation is placed on the thickness of the film layer except that the resultant film must rapidly dissolve in the mouth of the consumer. Therefore the thickness of the film can be varied based on, for example, the desired speed of dissolution of the edible film while in the oral cavity. Not only can the thickness be varied but a multi-layered film product may be provided.

After the coating step, the film may pass through a dryer for moisture reduction. In the dryer, drying is carried out through a variety of different means, such as high velocity turbulent hot air, conduction from steam heated slide bed, direct heating or casting of film onto a heated drum or belt, hot or cold air impingement, infrared heating, or any other suitable drying equipment that does not adversely affect the components of the film.

The edible thin films may then be processed to a desirable size to deliver a taste masking effective amount of the taste masking composition. In one embodiment, the edible thin films may be formed or cut as strips that are dimensioned to a desired size. For instance, the films may be 0.75 inch by 1.25 inch. While these dimensions illustrate that the film is cut as a rectangle, it is not limited thereto and any shape including, but not limited to, square, diamond, circular, elliptical, and a die cut of any predetermined shape. Procedures for forming or cutting the edible thin films are well known in the art.

Gummi Confectioneries

The edible gummi confectioneries, similarly to the edible thin films, are an edible composition designed to dissolve in the oral cavity in about 20 seconds or less (typically upon chewing) to provide the taste masking effect. The edible gummi confectioneries include a gelling agent to provide the confectionery composition with moldable and/or settable characteristics such that the confectionery can conform to the shape of a mold and thereafter retain that shape. In addition to the gelling agent, the confectionery composition for masking the taste of semen includes a physiological effective amount of a protein masking agent and a physiological effective amount of a bitter masking agent. The confectionery composition may also include a sensate, a flavoring agent, and/or a sweetening agent. It is understood that one or more of any of these individual ingredients may be used in a confectionery composition. For example, the composition may include one protein masking agent, two bitter masking agents, two sensates, one flavoring agent, and one sweetening agent as shown in Example 2 below.

Any suitable gelling agent can be used to produce a gummi confectionery product. Suitable film-formers include but are not limited to gelatin, gum arabic, pullulan, pectin, agar, carrageenan, clear gum, xanthan gum, alginic acid, alginates such as sodium alginate, potassium alginate, ammonium alginate, calcium alginate, locust bean gum, tapioca starch, konjac, ficus pumila, gellan gum, dextrin, maltodextrin, modified food starches, corn starch. In one embodiment, the concentration of the gelling agent constitutes between about 0.5% to about 30% dry weight, or about 1% to about 15% dry weight of the gummi confectionery.

The gelling agent is typically present in an aqueous solution. Accordingly, the gummi confectionery contains water as the balance of the composition. In one embodiment, the water may constitute about 40% to about 90%, or about 50% to 80% by weight of the gummi confectionery.

The edible gummi confectionery includes at least one protein masking agent. The protein masking agent may be any of the substances discussed above for the edible thin films. The protein masking agent may constitute about 0.01% to about 20%, or about 1% to about 15%, or about 5% to about 10% dry weight of the gummi confectionery.

The edible gummi confectionery includes at least one bitter masking agent. The bitter masking agent may be any of the substances discussed above for the edible thin films. The bitter masking agent is present in the film in an amount to mask the bitter taste of semen, especially when combined with the protein masking agent. In one embodiment, the bitter masking agent constitutes about 0.1% to about 7%, or about 0.5% to about 5% dry weight of the gummi confectionery.

The edible gummi confectionery may also include one or more sensates. The sensate may be a physiological cooling agent, a physiological warming agent, or a physiological tingling agent as discussed above for the edible thin films. The sensate(s) may constitute content about 0.1 to about 25%, or about 1% to about 15% dry weight of the gummi confectionery.

The edible gummi confectionery may also include one or more flavoring agents. The flavoring agents may be any of the substances discussed above for the edible thin films. Any suitable amount can be used in any sensorially acceptable fashion. In one embodiment, the flavoring agent can constitute about 0.1% to about 30%, or about 1% to about 20%, or about 5 to about 15% dry weight of the gummi confectionery.

Sweetening agents may also be used in the edible gummi confectionery. The sweetening agents may include any of the sweeteners and combinations thereof, discussed above for the edible thin films. In one embodiment, the sweetening agent constitutes about 1% to about 20%, or about 2% to about 15%, or about 10% dry weight of the gummi confectionery.

Additionally, the gummi confectionery may include other ingredients to provide desired characteristics to the composition. For example, coloring agents, preservatives, other thickening agents, emulsifiers, plasticizers, antioxidants, and combinations thereof may be added to the composition according to the same dry weights disclosed for the edible thin film.

Edible gummi confectionery may be manufactured by preparing molds, preparing a gummi confectionery composition, pouring the gummi confectionery composition in the mold, allowing the composition to set, and removing the set gummi confectionery from the mold. The gummi confectionery composition may be prepared by dissolving a gelling agent in water and heating to dissolve the gelling agent. To the gelling agent solution the taste masking agents, sensates, sweeteners, flavoring agents and any other ingredients may be added with mixing. The resulting gummi confectionery composition may be molded into desired shapes that will deliver the correct amount of the taste masking composition.

In another embodiment, the gummi confectionary may include a hydrocolloid ingredient in addition to the gelling agent. Suitable hydrocolloids include natural and modified gums, cellulosics, modified cellulosics, pectins, mucillages, modified starches, noncellulosic polysaccharides, algal polysaccharides and mixtures thereof. More specifically the hydrocolloids include starch, agar-agar, microcrystalline cellulose, methylcellulose, hydroxypropyl cellulose (HPC), hydroxypropyl methylcellulose (HPMC), xanthan gum, carrageenan gum, locust bean gum, alginates, acacia, carboxymethylcellulose (CMC), karaya gum, acacia gum, sodium alginate, sodium CMC, guar gum, tragacanth, mixtures of the hydrocolloids and the like.

When including a hydrocolloid, various ratios of gelatin/hydrocolloids have been discovered which have been found to possess beneficial mouthfeel, texture and chewing characteristics. For example, when using starch, the weight ratio of from about 1:1.3 to about 1:1.8 possesses desirable characteristics. More preferably the gelatin/starch weight ratio is from 1:1.4 to about 1:1.55 and most preferably the weight ratio is about 1:1.50. When agar-agar is used, the weight ratio is about 1:0.35 to about 1:1.5, preferably from 1:0.6 to about 1:1.2, and most preferably about 1:0.75. When employing hydroxypropylcellulose, the ratio is from about 1:0.2 to about 1:0.8, preferably the HPC/starch weight ratio is from about 1:0.3 to about 1:0.6 and most preferably the weight ratio is about 1:0.45. Those with skill in the art will recognize that other hydrocolloids can be used in combination with the specified hydrocolloids in the ratios specified, i.e., a mixture of two or more hydrocolloids, without departing from the present invention.

The edible taste masking compositions disclosed herein are useful for masking the taste of semen. Other applications for the taste masking compositions disclosed herein may include use as masking other substances that include a bitter component and/or a protein component.

The present invention is further illustrated by the following non-limiting examples.

Example 1

Edible Film for Masking the Taste of Semen

Part A: An aqueous solution of 40% gum arabic was prepared using standard techniques to dissolve the gum arabic in the water while heating and stirring.

Part B: An emulsion of a selected flavor, here mango citrus, was prepared by placing 80 ml of the 40% gum arabic solution into a blending vessel, weighting out selected flavors and an emulsifying agent, and slowly adding the flavors and emulsifying agent to the blending vessel with mixing. Once added, the mixing was maintained for about 20 additional minutes to form the emulsion. The dry weight percent for the ingredients added to the 40% gum arabic are presented below in Table 1.

TABLE 1

| Ingredient | Dry Wt % |
|---|---|
| emulsifying agent | 43 |
| mango flavoring | 28.5 |
| citrus flavoring | 28.5 |

Part C: The emulsion of the selected flavor was added to a film formulation. The film formulation was prepared as a slurry by mixing the following ingredients together using known techniques and then casting the film formulation onto a paper coated with or having a release surface so that the film will be removable therefrom. The slurry includes 10 grams of water and the amount of the remaining ingredients as indicated below in Table 2 in dry weight percent based on the final film produced.

TABLE 2

| Ingredient | Dry Wt % |
|---|---|
| corn starch | 27.8 |
| modified tapioca starch | 9.3 |
| pullulan solution, 6.5% | 1.2 |
| polysorbate 80 | 4.6 |
| sorbitol solution, 70% | 3.3 |
| gelatin solution, 30% | 14 |
| the emulsion of flavors from Part B | 11.5 |
| cooling agent | 13.9 |
| protein masker | 0.5 |
| bitter masker* | 4.6 |
| vanilla syrup | 9.3 |

The bitter masker included a first bitter masker and a second bitter masker at 1.8 dry weight percent and 2.8 dry weight percent, respectively.

Part D: The slurry from Part C is cast onto the release paper by a knife over roll coater set at a coating gap of 13 mil at a line speed of 1-3 fpm while the slurry is warm (about 104° F. (40° C.)). The release paper coated with the slurry passed through an oven at a temperature of about 180 to 200° F. (356-392° C.) to evaporate the water and form a film.

The resulting film may be cut to any desired dimensions for packaging and/or consumption that provides the correct amount of the formulation for the desired extended taste masking effect.

Example 2

Edible Film for Masking the Taste of Semen

An aqueous solution of 40% gum arabic was prepared according to Part A of Example 1 using standard techniques to dissolve the gum arabic in the water while heating and stirring.

Part B: Then an emulsion of a selected flavor, here watermelon, was prepared by placing 80 ml of the 40% gum arabic solution into a blending vessel, weighting out selected flavor and an emulsifying agent, and slowly adding the flavors and emulsifying agent to the blending vessel with mixing. Once added, the mixing was maintained for about 20 additional minutes to form the emulsion. The dry weight percent for the ingredients added to the 40% gum arabic are presented below in Table 3.

TABLE 3

| Ingredient | Dry Wt % |
|---|---|
| emulsifying agent | 43 |
| Watermelon flavoring | 43 |

Part C: The emulsion of the selected flavor was added to a film formulation. The film formulation was prepared as a slurry by mixing the following ingredients together using known techniques and then casting the film formulation onto a paper coated with or having a release surface so that the film will be removable therefrom. The slurry includes 10 grams of water and the amount of the remaining ingredients as indicated below in Table 4 in dry weight percent based on the final film produced.

TABLE 4

| Ingredient | Dry Wt % |
|---|---|
| modified food starch | 18 |
| dextrin | 10.7 |
| pullulan | 5 |
| polysorbate 80 | 3 |
| glycerin | 3 |
| gelatin | 5 |
| the emulsion of flavors from Part B | 25 |
| cooling agent | 2 |
| protein masker 1 | 4 |
| bitter masker | 6 |
| vanilla syrup | 5 |
| protein masker 2 | 10 |
| tingler | 1 |
| FD&C Blue 1 | 0.1 |
| FD&C Yellow 5 | 0.2 |
| Sweetener | 2 |
| Total: | 100 |

Part D: The slurry from Part C is cast onto the release paper by a knife over roll coater set at a coating gap of 13 mil at a line speed of 1-3 fpm while the slurry is warm (about 104° F. (40° C.)). The release paper coated with the slurry passed through an oven at a temperature of about 180 to 200° F. (356-392° C.) to evaporate the water and form a film.

The resulting film may be cut to any desired dimensions for packaging and/or consumption that provides the correct amount of the formulation for the desired extended taste masking effect.

Example 3

Edible Film for Masking the Taste of Semen

Part A: An aqueous solution of 40% gum arabic was prepared using standard techniques to dissolve the gum arabic in the water while heating and stirring.

Part B: An emulsion of a selected flavor, here vanilla, was prepared by placing 80 ml of the 40% gum arabic solution into a blending vessel, weighting out selected flavor and an emulsifying agent, and slowly adding the flavors and emulsifying agent to the blending vessel with mixing. Once added, the mixing was maintained for about 20 additional minutes to form the emulsion. The dry weight percent for the ingredients added to the 40% gum arabic are presented below in Table 5.

TABLE 5

| Ingredient | Dry Wt % |
| --- | --- |
| emulsifying agent | 43 |
| vanilla flavoring | 43 |

Part C: The emulsion of the selected flavor was added to a film formulation. The film formulation was prepared as a slurry by mixing the following ingredients together using known techniques and then casting the film formulation onto a paper coated with or having a release surface so that the film will be removable there from. The slurry includes 10 grams of water and the amount of the remaining ingredients as indicated below in Table 6 in dry weight percent based on the final film produced.

TABLE 6

| Ingredient | Dry Wt % |
| --- | --- |
| modified food starch | 18 |
| maltodextrin | 18 |
| agar-agar | 2 |
| polysorbate 80 | 3 |
| glycerin | 3 |
| gelatin | 4 |
| the emulsion of flavors from Part B | 22 |
| cooling agent 1 | 1 |
| protein masker 1 | 3 |
| bitter masker | 6 |
| vanilla syrup | 4.4 |
| protein masker 2 | 6 |
| tingler | 0.5 |
| FD&C Blue 1 | 0.1 |
| cooling agent 2 | 5 |
| Sweetener | 4 |
| Total: | 100 |

Part D: The slurry from Part C is cast onto the release paper by a knife over roll coater set at a coating gap of 13 mil at a line speed of 1-3 fpm while the slurry is warm (about 104° F. (40° C.)). The release paper coated with the slurry passed through an oven at a temperature of about 180 to 200° F. (356-392° C.) to evaporate the water and form a film.

The resulting film may be cut to any desired dimensions for packaging and/or consumption that provides the correct amount of the formulation for the desired extended taste masking effect.

Example 4

Edible Gummi Confectionery for Masking the Taste of Semen

Part A: Confectionery molds were prepared by spraying the selected molds with a non-stick cooking spray. The molds are of a size that provides the correct amount of the formulation for the desired extended taste masking effect.

Part B: A mango citrus flavor emulsion was prepared as disclosed in Example 1, Part B.

Part C: A gummi confectionery mixture was prepared by boiling 45 grams of water in a saucepan over medium-high heat and immediately upon boiling adding 30 grams of gelatin with mixing until all dissolved. Once the gelatin was dissolved, 0.5 grams of polysorbate 80, 3.3 grams of the mango citrus flavor emulsion, 1.5 grams of coolants, 0.05 grams of a protein masker, 0.5 grams of a bitter masker, and 2 grams of vanilla syrup were added to the dissolved gelatin with stirring until a homogenous mixture was formed.

Part D: The mixture from Part C was poured into the molds prepared in Part A. The molds were refrigerated until the gummi confectioneries were set. Once removed from the molds, the confectioneries were ready for consumption.

Example 5

Alpha Survey Evaluation of the Lasting Taste Masking Effect

An alpha survey was run on 21 test subjects. The purpose of the alpha survey was to evaluate the taste masking film strip for taste masking effectiveness in masking the taste of semen. The test group was composed of both male and female subjects. The test subject placed the taste masking film strip in their mouth on the middle of their tongue, and after the film strip dissolved in their mouth performed oral sex on their partner. The test subjects evaluated how many minutes of taste masking effectiveness was delivered by the film strip. Table 7 shows the taste masking effectiveness of the film strip in masking the taste of semen for the 21 test subjects.

TABLE 7

| Taste Masking Effectiveness in Minutes | |
| --- | --- |
| Test Subject | Time |
| 1 | 11 min. |
| 2 | 6 min. |
| 3 | 8 min. |
| 4 | 19 min. |
| 5 | 14 min. |
| 6 | 7 min. |
| 7 | 12 min. |
| 8 | 8 min. |
| 9 | 10 min. |
| 10 | 9 min. |
| 11 | 16 min. |
| 12 | 6 min. |
| 13 | 11 min. |
| 14 | 8 min. |
| 15 | 7 min. |
| 16 | 17 min. |
| 17 | 9 min. |
| 18 | 7 min. |
| 19 | 14 min. |
| 20 | 13 min. |
| 21 | 9 min. |

The taste masking effectiveness of the film strip to mask the taste of semen was found to last for about five to about twenty minutes. The data above reflects how long the taste masking effect lasted relative to the release of semen. The subjects stopped the clock once the semen was introduced, even though the taste masking effect may actually have lasted longer. The importance of the data is that for those men who took longer to be stimulated, 14 to 19 minutes (Test subjects 4, 5, 11, 16, and 19), the taste masking was still in effect for the partner.

Having described the invention in detail and with reference to specific advantages thereof it will be apparent that numerous modifications are possible without departing from the spirit and scope of the following claims.

What is claimed is:

1. An edible film comprising;
    a film former having included therein:
        a sweetener comprising an amount that is about 2% to about 20% dry weight of the edible film;
        a non-skin irritating protein masking agent comprising an amount that is about 0.5% to about 16% dry weight of the edible film, wherein the non-skin irritating protein masking agent is an oil soluble liquid natural flavoring that masks the taste of animal protein and has a sausage-like odor and flavor, a density of 0.899 to 0.959 g/ml at 25° C., and a yellow color;
        a non-skin irritating bitter masking agent comprising an amount that is about 0.1% to about 7% dry weight of the edible film;
        a non-skin irritating sensate comprising an amount that is about 1% to about 25% dry weight of the edible film, wherein the non-skin irritating sensate comprises a physiological cooling agent; and
        a non-skin irritating flavoring agent;
    wherein a single edible film, upon activation in saliva in a user's oral cavity, provides a lasting taste masking effect to mask the taste of semen that endures for about 5 minutes to about 20 minutes.

2. The edible film of claim 1 wherein the lasting taste masking effect endures for about 9 to about 20 minutes.

3. The edible film of claim 1, wherein the film former is selected from the group consisting of carboxymethylcellulose, methylcellulose, hydroxypropylmethylcellulose, guar gum, locust bean gum, xanthum gum, carrageenan, algins, propylene glycol, levan, elsinan, pullulan, pectin, chitosan, and gum arabic, waxy maize starch, high-amylose corn starch, potato starch, tapioca starch, rice starch, wheat starch, a modified starch, dextrin, maltodextrin, albumen, gelatin, casein, salts of casein, whey, wheat gluten, zein, and soybean-derived protein, polyvinyl pyrrolidone, methycrylate copolymers, carboxyvinyl copolymers, and combinations thereof.

4. The edible film of claim 1 wherein the non-skin irritating flavoring agent constitutes about 0.1% to about 30% dry weight of the edible film.

5. The edible film of claim 1, wherein the non-skin irritating bitter masking agent includes one or more of a hydrogenated, ethoxylated glycerol ester, an adenosine 5'-monophosphate, a thymidine 5'-monophosphate, an adenosine 5'-diphosphate, an adenosine 3'-monophosphate, an adenosine 5'-succinate, an adenosine 5'-triphosphate, an adenosine 2'-monophosphate, a 5'-cytidylic acid, an inosinic acid, a glyceryl dipalmitostearate, a glycerol monostearate, a monoglyceride, a diglyceride, a glycerol distearate, and a glyceryl di stearate.

6. The edible film of claim 1, wherein the non-skin irritating sensate further comprises a physiological tingling agent and a physiological warming agent.

7. The edible film of claim 1 wherein the lasting taste masking effect endures for about 14 to about 20 minutes.

8. The edible film of claim 1, wherein the non-skin irritating bitter masking agent comprises a mixture of a hydrogenated, ethoxylated glycerol ester and a bitter masking agent selected from the group of adenosine 5'-monophopshate, thymidine 5'-monophosphate, adenosine 5'-diphosphate, adenosine 3'-monophopshate, adenosine 5'-succinate, adenosine 5'-triphosphate, adenosine 2'-monophosphate, 5'-cytidylic acid, and inosinic acid.

* * * * *